(12) United States Patent
Aoyama et al.

(10) Patent No.: US 7,862,965 B2
(45) Date of Patent: Jan. 4, 2011

(54) METHOD FOR DETECTING DEFECTS WHICH ORIGINATE FROM CHEMICAL SOLUTION AND METHOD OF MANUFACTURING SEMICONDUCTOR DEVICE

(75) Inventors: Hisako Aoyama, Yokohama (JP); Yuji Kobayashi, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 850 days.

(21) Appl. No.: 11/797,529

(22) Filed: May 4, 2007

(65) Prior Publication Data

US 2008/0014535 A1 Jan. 17, 2008

(30) Foreign Application Priority Data

May 11, 2006 (JP) .............................. 2006-132765

(51) Int. Cl.
*G03F 9/00* (2006.01)
*G03C 5/00* (2006.01)
(52) U.S. Cl. ........................ 430/30; 430/311; 430/312; 430/328; 382/144; 382/145
(58) Field of Classification Search .................... 430/30, 430/311, 312, 328; 382/144, 145
See application file for complete search history.

(56) References Cited

U.S. PATENT DOCUMENTS

2004/0246479 A1   12/2004   Cartlidge et al.

FOREIGN PATENT DOCUMENTS

JP          2005-300421         10/2005

*Primary Examiner*—Christopher G Young
(74) *Attorney, Agent, or Firm*—Finnegan, Henderson, Farabow, Garrett & Dunner, L.L.P.

(57) ABSTRACT

A method for detecting defects which originate from a chemical solution includes coating a chemical solution on a surface of a mask, and radiating an exposure beam to the mask on which the chemical solution is coated, thereby performing enlarged projection exposure on a resist film which is formed on a surface of a substrate for an inspection. Further, the method for detecting defects which originate from a chemical solution includes performing an inspection of defects on the resist film which has been subjected to the enlarged projection exposure, and determining whether a result of the inspection meets a predetermined standard.

5 Claims, 3 Drawing Sheets

METHOD FOR DETECTING DEFECTS WHICH ORIGINATE FROM CHEMICAL SOLUTION AND METHOD OF MANUFACTURING SEMICONDUCTOR DEVICE

CROSS-REFERENCE TO RELATED APPLICATIONS

This application is based upon and claims the benefit of priority from prior Japanese Patent Application No. 2006-132765, filed May 11, 2006, the entire contents of which are incorporated herein by reference.

BACKGROUND OF THE INVENTION

1. Field of the Invention

The present invention relates to a method for detecting defects which originate from a chemical solution that is used in a semiconductor fabrication process, and a method of manufacturing a semiconductor device.

2. Description of the Related Art

In the prior art, in order to ensure the quality of a chemical solution for a resist, the chemical solution has been tested by using a particle-in-liquid counter (see, e.g. Jpn. Pat. Appln. KOKAI Publication No. 2005-300421). Thereby, particles in the chemical solution are measured on a size-by-size basis, and the quality of the chemical solution is managed on the basis of the measurement result. Specifically, the resist chemical solution is let to flow through a light-transmissive fine tube in a downward direction from above. By radiating light and observing scattered light, the presence/absence of particles is measured.

However, in the case where particles in the chemical solution are measured by the conventional method, only particles with a diameter of 0.15 μm or more can be measured at present. In other words, the number of fine particles with a diameter of, e.g. 0.05 μm to 0.15 μm, which need to be measured in actual fabrication of devices, cannot be managed.

In addition, defects, which are observed when a resist pattern is fabricated on a semiconductor substrate, do not always correspond to foreign matter which can be monitored by the particle-in-liquid counter. It is thus desirable that a defect inspection be performed by a defect inspection device after a desired resist pattern is formed on the semiconductor substrate.

However, the size of defects, which can be detected by the defect inspection device, is limited by the specifications of the inspection device. On the other hand, there is a trend that the device size will further decrease. It is thus necessary to detect a defect which occurs when a resist pattern is formed on the semiconductor substrate, and which has such a size as to affect a yield but cannot be observed by the conventional defect inspection device.

BRIEF SUMMARY OF THE INVENTION

According to a first aspect of the present invention, there is provided a method for detecting defects which originate from a chemical solution, comprising: coating a chemical solution on a surface of a mask; radiating an exposure beam to the mask on which the chemical solution is coated, thereby performing enlarged projection exposure on a resist film which is formed on a surface of a substrate for an inspection; performing an inspection of defects on the resist film which has been subjected to the enlarged projection exposure; and determining whether a result of the inspection meets a predetermined standard.

According to a second aspect of the present invention, there is provided a method of manufacturing a semiconductor device, comprising: coating a chemical solution, which is used as a resist, on a surface of a mask; radiating an exposure beam to the mask on which the chemical solution is coated, thereby performing enlarged projection exposure on a resist film which is formed on a surface of a substrate for an inspection; performing an inspection of defects on the resist film which has been subjected to the enlarged projection exposure; determining whether a result of the inspection meets a predetermined standard; coating, in a case where the standard is met, the chemical solution on a processing-object substrate as a resist solution, thereby forming a resist film for pattern formation; exposing the resist film for pattern formation; and developing the resist film for pattern formation, thereby forming a resist pattern.

DETAILED DESCRIPTION OF THE INVENTION

Figure 1:
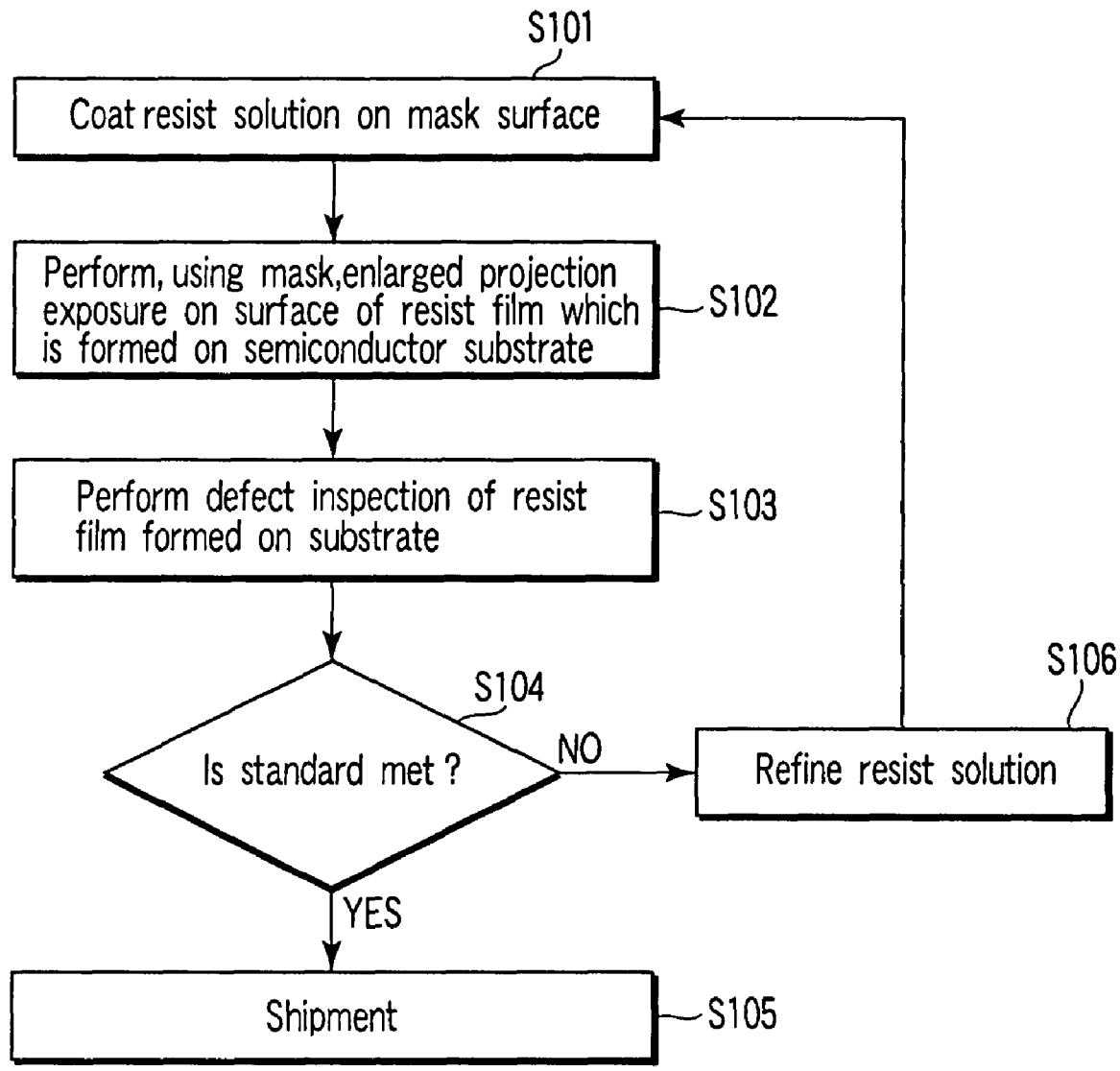
FIG. 1 is a flow chart of a method for detecting defects originating from a chemical solution according to a first embodiment.

Embodiments of the present invention will now be described with reference to the accompanying drawings. In the description below, elements having the same functions are denoted by like reference numerals.

First Embodiment

A method for detecting defects of a chemical solution according to a first embodiment of the present invention is described with reference to a flow chart of FIG. 1.

Figure 2:
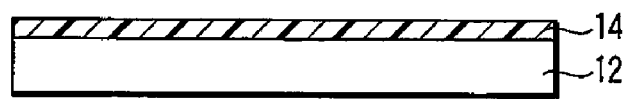
FIG. 2 illustrates a fabrication step of the method for detecting defects originating from a chemical solution according to the first embodiment.

A resist solution, which is a chemical solution for use in photolithography, for example, a chemically amplified resist solution for ArF, is coated on the surface of, e.g. a glass mask 12 which is used as a photomask (step S101). The glass mask 12 is formed of, e.g. quartz, and no pattern is formed on the glass mask 12. At this time, in order to eliminate causes of defects, other than those originating from the resist solution, the resist solution is coated in the as clean as possible state. After the coating, the structure is subjected to heat treatment. Thus, a resist film 14 is formed on the surface of the glass mask 12, as shown in FIG. 2.

Figure 3:
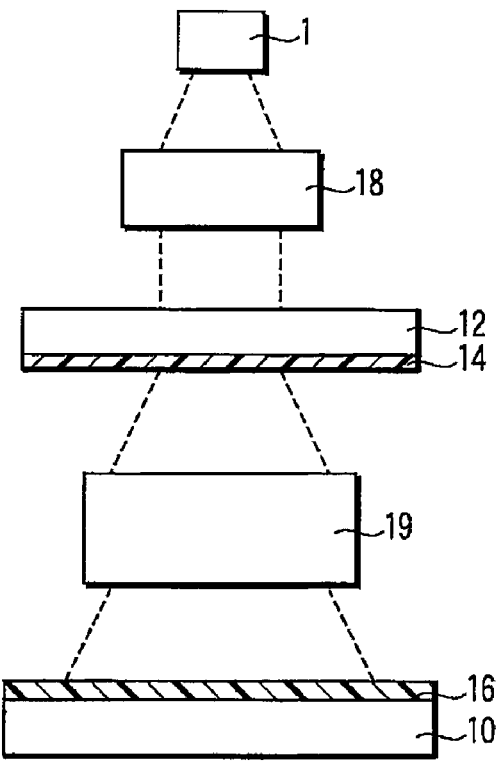
FIG. 3 illustrates a fabrication step, following the fabrication step shown in FIG. 2, of the method for detecting defects originating from a chemical solution.

Using the glass mask 12, on the surface of which the resist film 14 is formed, enlarged projection exposure is performed by an exposure device on a semiconductor substrate 10 (substrate for an inspection) on the surface of which another resist film 16 is formed, as shown in FIG. 3 (step S102). The exposure device shown in FIG. 3 includes, for example, a light source 1, a condenser lens 18 and a projection lens 19. The exposure is performed, for example, by a step-and-repeat method or a scan-and-repeat method, and a mask is transferred to the other resist mask 16, with a magnification being set at, e.g. 10.

Figure 4:
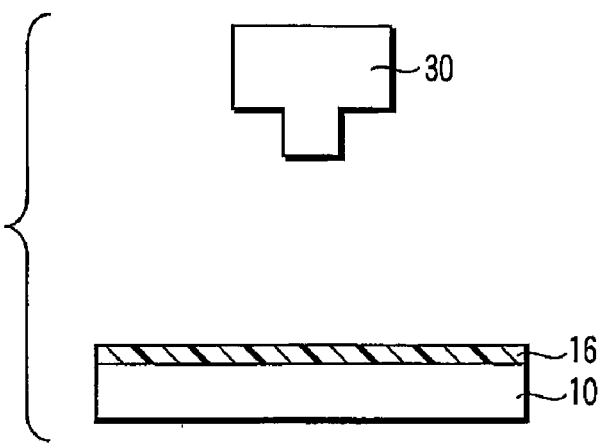
FIG. 4 illustrates a fabrication step, following the fabrication step shown in FIG. 3, of the method for detecting defects originating from a chemical solution.

Subsequently, the other resist film 16 on the semiconductor substrate 10, which has been subjected to enlarged projection exposure, is developed, and a defect inspection of the other resist film 16 is performed by a defect inspection device 30, as shown in FIG. 4 (step S103). The defect inspection device 30 is, for example, an SEM (Scanning Electron Microscope), a CCD camera, an image analysis device, or a combination thereof. The defect inspection device 30 can automatically count defects of a size or more, which is predetermined by specifications, etc. of the device.

A defect in the other resist film 16 corresponds to a defect in the resist film 14, which is enlarged by the projection lens 19. Accordingly, by performing a defect inspection of the other resist film 16, it is possible to perform an inspection for detecting a defect in the resist solution, of which the resist film 14 is formed.

It is determined whether the result of the defect inspection meets a predetermined standard, for example, whether the number of defects of a certain size or more on the other resist film 16 on the substrate 10 is a predetermined number or less (step S104). This standard may be set, for example, so as to achieve a desired yield for the formation of patterns with specified precision.

If the above standard is met, the resist solution is shipped (step S105). However, if it is determined that the standard is not met, refinement of the resist solution, for example, filtering, is performed (step S106), and the resist solution is coated once again on the mask and a similar inspection is repeated.

Figure 5:
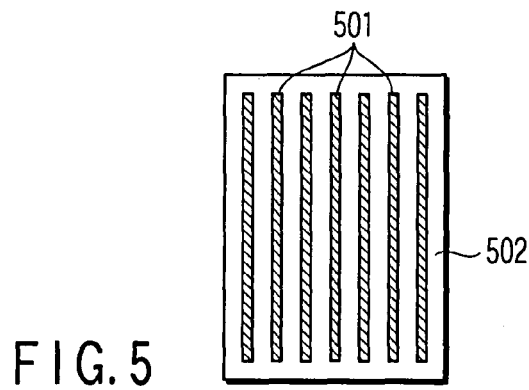
FIG. 5 shows a photomask which is used in another example of the method for detecting defects originating from a chemical solution according to the first embodiment.

In the present embodiment, the transparent glass mask 12, on which no pattern is formed, is used as a mask on which the resist solution, a defect of which is to be inspected, is coated. Alternatively, a mask on which a pattern is formed in advance may be used, as shown in FIG. 5.

For example, when a pattern of lines and spaces of 45 nm is to be formed, there is such a case that a defect with a diameter of 10 nm is tolerated even if the defect is transferred to the resist film, but a defect with a diameter of 35 nm cannot be tolerated. In such a case, a glass mask 502 on which a line pattern 501 is formed, as shown in FIG. 5, is used as a mask. A resist solution is coated on this mask and a resist film is formed. Thereafter, the enlarged projection exposure is performed.

In step S104, the surface of the other resist film 16 on the semiconductor substrate 10, which has been subjected to the enlarged projection exposure, is imaged by, e.g. a CCD camera, and the obtained image is processed by an image analysis device. In a case where an intolerable defect is present in the resist solution that is the object of the inspection, lines of the transferred pattern are connected to each other or are likely connected to each other. Based on the image, the image analysis device determines that the standard is not met. In this manner, the standard for determining the quality of the resist solution may be provided on the mask.

Normally, it is desirable that the defect inspection in the lithography step of the semiconductor fabrication process be performed by the defect inspection device after a desired resist pattern is formed on the semiconductor substrate. However, in the prior art, in the case of a defect originating from a resist solution, the defect has been managed by the particle-in-liquid counter, because of the inadequacy of the inspection environment and a great deal of time that is necessary for the inspection.

However, in the measurement of the number of foreign matters in the resist solution by the particle-in-liquid counter, the size of the measurable foreign matter is limited, and fine foreign matter, which must be detected for device fabrication, cannot be measured. Moreover, there is the disadvantage that defects of the resist pattern which is formed on the semiconductor substrate, even if such defects originate from the resist material, cannot always be monitored by the particle-in-liquid counter because of the size and shape of defects.

In the present embodiment, the resist solution is coated on the mask and the defects in the resist are subjected to enlarged projection exposure. Thereby, the detection of defects on the semiconductor substrate can easily be performed by directly using the conventional defect inspection device.

Thereby, it becomes possible to perform the detection of fine foreign matter which cannot conventionally be detected by the particle-in-liquid counter that is usually used in the quality evaluation of the resist solution, and to perform the detection of detects originating from the resist material, which cannot be evaluated by the particle-in-liquid counter.

Furthermore, it becomes possible to detect fine foreign matter which has not been detectable by the defect inspection device, because of the fineness of the fine foreign matter, after the resist pattern is formed on the substrate by using the resist solution including the fine foreign matter. Therefore, if the re-refinement of the resist solution is performed by using the defect detection method of this embodiment, the quality of the chemical solution can be improved.

In the present embodiment, the resist solution has been exemplified as the chemical solution. However, other examples of the chemical solution may include a chemical solution for an ARC (Anti-Reflective Coating), a low-dielectric-material-containing solution, and a ferroelectric-material-containing solution.

Second Embodiment

Figure 6:
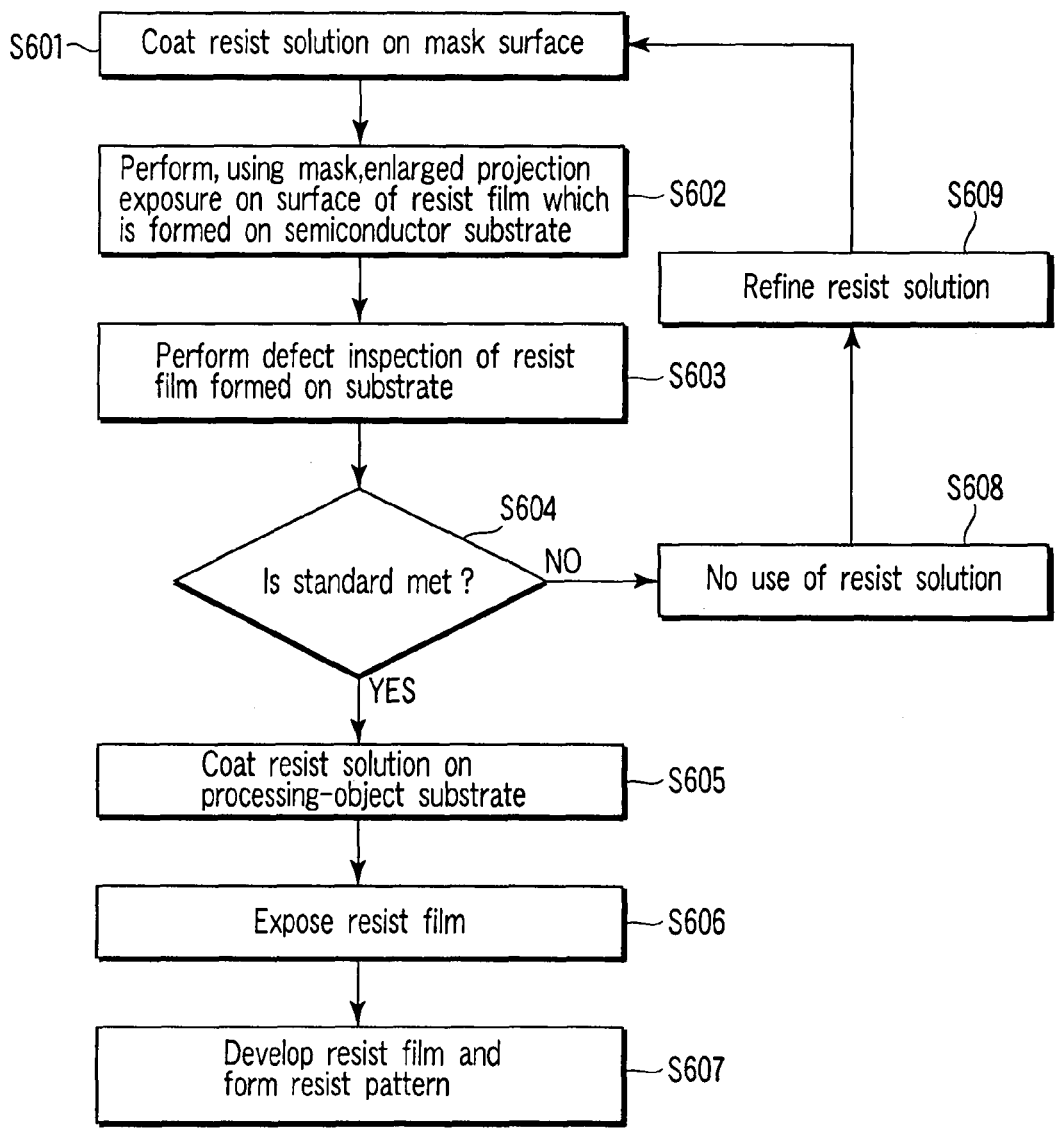
FIG. 6 is a flow chart of a method of manufacturing a semiconductor device according to a second embodiment.

A method of manufacturing a semiconductor device according to a second embodiment of the present invention is described with referring to a flow chart of FIG. 6.

Steps S601 to S604 of the method of manufacturing the semiconductor device according to the present embodiment are the same as steps S101 to S104, shown in FIG. 1, of the method for detecting defects in a chemical solution according to the first embodiment.

In step S604, like the first embodiment, it is determined whether the result of the defect inspection meets the predetermined standard. This standard is, for example, a standard for determining whether the number of defects of a certain size or more on the other resist film 16 on the substrate 10 for the inspection, as shown in FIG. 3, is a predetermined number or less. This standard may be set so as to achieve a desired yield for the formation of patterns with specified precision.

If the above standard is met, the resist solution is coated by a resist coating step on a semiconductor substrate which is a processing-object substrate on which an underlying structure is formed in advance (step S605). Further, the resultant structure is subjected to heat treatment, and a resist film is formed.

Subsequently, using a mask on which a desired pattern is formed, the resist film is exposed (step S606) and developed to form a desired resist pattern (step S607). Thereafter, an etching step and a resist-removing step are carried out, and a desired pattern is formed on the processing-object substrate.

On the other hand, if it is determined in step S604 that the standard is not met, the resist solution is not used (step S608) and is re-refined (step S609).

According to the present embodiment, the number of defects, which include foreign particles mixed in the resist solution in the step of coating the resist solution on the processing-object substrate, is set at a standard or less, which is necessary for achieving a predetermined yield. In other words, the resist solution, which is suitable for the manufacture of the device with desired precision, is selected.

It is thus possible to reduce the problems such as line short-circuit in a line-based pattern and an aperture defect in a contact-hole-based pattern, which originate from defects of the resist solution. Therefore, the reliability of the device can be increased and the yield can be improved.

According to an aspect of the present invention, there can be provided a method for detecting defects originating from a chemical solution, the method being able to detect foreign matter in the chemical solution which may cause such fine defects as to be undetectable by a conventional resist pattern defect inspection device.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of manufacturing a semiconductor device, comprising:

coating a chemical solution, which is used as a first resist film, on a surface of a mask;

radiating an exposure beam to the mask on which the chemical solution is coated, thereby performing enlarged projection exposure on a second resist film which is formed on a surface of a substrate for an inspection;

performing an inspection of defects on the second resist film which has been subjected to the enlarged projection exposure;

determining whether a result of the inspection meets a predetermined standard;

coating, in a case where the standard is met, the chemical solution on a processing-object substrate as a resist solution, thereby forming a third resist film for pattern formation;

exposing the third resist film for pattern formation; and developing the third resist film for pattern formation, thereby forming a resist pattern.

2. The method according to claim 1, wherein the mask is a glass mask, or a pattern is formed in advance on the mask.

3. The method according to claim 1, wherein a line-and-space pattern is formed in advance on the mask.

4. The method according to claim 1, wherein the chemical solution is a chemically amplified resist solution for ArF.

5. The method according to claim 1, wherein in the inspection, use is made of an SEM (Scanning Electron Microscope), a CCD (Charge-Coupled Device) camera, an image analysis device, or a combination thereof.

* * * * *